US009688606B2

(12) United States Patent
Neto et al.

(10) Patent No.: US 9,688,606 B2
(45) Date of Patent: *Jun. 27, 2017

(54) PROCESS FOR ACIDIC SCRUBBING OF DINITROTOLUENE IN THE PRESENCE OF HYDROCYANIC ACID

(71) Applicants: BASF SE, Ludwigshafen (DE); Josef Meissner GmbH & Co. KG, Köln (DE)

(72) Inventors: Samuel Neto, Manila (PH); Rüdiger Fritz, Bernsdorf (DE); Renate Hempel, Ruhland (DE); Holger Allardt, Schwarzheide (DE); Yuan Shen Dai, Mannheim (DE); Barbara Becker, Moerlenbach (DE); Sebastian Ahrens, Weisenheim am Sand (DE); Julia Leschinski, Weiterstadt (DE); Henrich Hermann, Köln (DE); Mirko Haendel, Neunkirchen-Seelscheid (DE); Jürgen Pöhlmann, Köln (DE)

(73) Assignees: BASF SE (DE); Josef Meissner GmbH & Co. KG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/031,100

(22) PCT Filed: Oct. 22, 2014

(86) PCT No.: PCT/EP2014/072633
§ 371 (c)(1),
(2) Date: Apr. 21, 2016

(87) PCT Pub. No.: WO2015/059185
PCT Pub. Date: Apr. 30, 2015

(65) Prior Publication Data
US 2016/0251302 A1  Sep. 1, 2016

(30) Foreign Application Priority Data

Oct. 22, 2013 (EP) .................................. 13189687

(51) Int. Cl.
*C07C 201/16* (2006.01)
*C07C 205/06* (2006.01)
(Continued)

(52) U.S. Cl.
CPC ........ *C07C 201/16* (2013.01); *B01D 11/0488* (2013.01); *B01D 11/0492* (2013.01);
(Continued)

(58) Field of Classification Search
CPC .... C07C 205/06; C07C 201/06; C07C 201/16
(Continued)

(56) References Cited

U.S. PATENT DOCUMENTS 2,976,320 A    3/1961  Winstrom et al.
3,162,510 A   12/1964  Meissner et al.
(Continued)

FOREIGN PATENT DOCUMENTS

CA    1 034 603 A    7/1978
CA    2871543 A1    10/2013
(Continued)

OTHER PUBLICATIONS

International Preliminary Examination Report for PCT/EP2014/072633 mailed Sep. 30, 2015.
(Continued)

*Primary Examiner* — Jafar Parsa
(74) *Attorney, Agent, or Firm* — Drinker Biddle & Reath LLP

(57) ABSTRACT

Process for scrubbing a crude mixture which is obtained in the nitration of toluene after separating off the nitrating acid
(Continued)

and comprises dinitrotoluene, nitric acid, nitrogen oxides and sulfuric acid, which comprises two scrubbing steps (WS-I) and (WS-II), wherein i) in a first scrubbing step (WS-I), the crude mixture is extracted with a scrubbing acid I comprising nitric acid, nitrogen oxides and sulfuric acid in a scrub comprising at least one extraction stage, where the scrubbing acid discharged from the first extraction stage (WS-I-1) of the first scrubbing step (WS-I) has a total acid content of from 10 to 40% by weight and a content of from 80 to 350 ppm of hydrocyanic acid, giving a prescrubbed crude mixture, ii) in a second scrubbing step (WS-II), the prescrubbed crude mixture comprising dinitrotoluene is extracted with a scrubbing acid II in a scrub comprising at least one, preferably at least 2, extraction stage(s), where the scrubbing acid discharged from the first extraction stage (WS-II-1) of the second scrubbing step (WS-II) has a pH of less than or equal to 4, giving a dinitrotoluene-comprising mixture which is essentially free of nitric acid, sulfuric acid, nitrogen oxides and hydrocyanic acid and has a content of not more than 300 ppm of nitric acid and nitrogen oxides, not more than 3 ppm of sulfate and not more than 50 ppm of hydrocyanic acid.

15 Claims, 2 Drawing Sheets

(51) Int. Cl.
*B01D 11/04* (2006.01)
*C02F 1/20* (2006.01)
*C02F 1/26* (2006.01)
*C02F 3/00* (2006.01)
*B01D 11/00* (2006.01)
*C02F 101/18* (2006.01)
*C02F 103/36* (2006.01)

(52) U.S. Cl.
CPC .................. *C02F 1/20* (2013.01); *C02F 1/26* (2013.01); *C02F 3/00* (2013.01); *B01D 2011/002* (2013.01); *C02F 2101/18* (2013.01); *C02F 2103/36* (2013.01)

(58) Field of Classification Search
USPC .................................................. 568/924, 927
See application file for complete search history.

(56) References Cited

U.S. PATENT DOCUMENTS

| | | |
|---|---|---|
| 4,361,712 A | 11/1982 | Herman et al. |
| 4,482,769 A | 11/1984 | Toseland et al. |
| 4,597,875 A | 7/1986 | Carr et al. |
| 5,001,286 A | 3/1991 | Witt et al. |
| 5,756,867 A | 5/1998 | Hermann et al. |
| 6,288,289 B1 | 9/2001 | Boyd et al. |
| 7,470,826 B2 | 12/2008 | Hermann et al. |

FOREIGN PATENT DOCUMENTS

| | | |
|---|---|---|
| DE | 1 135 425 B | 8/1962 |
| EP | 0 279-312 A2 | 8/1988 |
| EP | 0736514 A1 | 10/1996 |
| EP | 1780195 A1 | 5/2007 |
| WO | WO-2013160367 A1 | 10/2013 |

OTHER PUBLICATIONS

International Search Report for PCT/EP2014/072633 mailed Jan. 7, 2015.
English Translation of International Preliminary Report on Patentability issued in corresponding foreign application PCT/EP2014/072633 dated Feb. 25, 2016.

PROCESS FOR ACIDIC SCRUBBING OF DINITROTOLUENE IN THE PRESENCE OF HYDROCYANIC ACID

CROSS-REFERENCE TO RELATED APPLICATIONS

This application is a national stage application (under 35 U.S.C. §371) of PCT/EP2014/072633, filed Oct. 22, 2014, which claims benefit of European Application No. 13189687.0, filed Oct. 22, 2013, both of which are incorporated herein by reference in their entirety.

The invention relates to a process for scrubbing a crude mixture which is obtained in the nitration of toluene after separating off the nitrating acid and comprises dinitrotoluene (DNT), nitric acid, nitrogen oxides and sulfuric acid.

The present invention relates in particular to a process for scrubbing the DNT-comprising crude mixture (hereinafter also referred to as crude DNT) from a continuous isothermal nitration of toluene to form DNT in a mixture of sulfuric acid and nitric acid, which process allows the scrubbing water resulting from this scrub to be subjected after removal of DNT and hydrocyanic acid dissolved in this water, without any further physical or chemical pretreatment, to biological treatment in a water treatment plant, with the wastewater discharged from the water treatment plant meeting the requirements in respect of toxicity as are prescribed in, for example, the wastewater regulations of the Federal Republic of Germany, appendix 22: Chemische Industrie.

The continuous isothermal or adiabatic nitration of toluene to form DNT in one or two stages in countercurrent using mixed acid always gives, after phase separation, a crude nitroaromatic product which has to be freed of the impurities dissolved therein before further use. Apart from the final nitrating acid composed of nitric acid, sulfuric acid and nitrogen oxides dissolved in the nitroaromatic or present as microemulsion, oxidation products from secondary reactions with the aromatic to be nitrated, e.g. mononitrocresols, dinitrocresols and trinitrocresols or aromatic carboxylic acids such as mononitrobenzoic and dinitrobenzoic acids (hereinafter referred to as nitrobenzoic acids or NBAs) and degradation products thereof, are also comprised in the crude DNT.

The nitration of toluene to form dinitrotoluenes results in the formation of, inter alia, mononitrocresols (MNC), dinitrocresols (DNC) and trinitrocresols (TNC), trinitrophenol (picric acid PA), nitrobenzoic acids such as mononitrobenzoic acid (MNBA) and dinitrobenzoic acid (DNBA), oxidative degradation products of the traces of aliphatic/cycloaliphatic hydrocarbons present in the toluene, of nitrocresols and nitroaromatics, e.g. carbon dioxide ($CO_2$), carbon monoxide (CO), hydrocyanic acid (HCN), tetranitromethane (TNM), formic acid, acetic acid and oxalic acid, and reduction products of nitric acid, e.g. nitrogen oxides ($NO_2$/NO) and dinitrogen oxide ($N_2O$), which can all be dissolved in the nitrotoluene (MNT, DNT) after removal of the final nitrating acid, as by-products in addition to the desired nitro compounds.

The formation of all these by-products and degradation products does not occur to the same extent in all nitration stages but instead depends, like the preferred formation of the individual nitroaromatics, too, on the water content of the mixed acid. Thus, for example, the mononitrocresols and dinitrocresols are formed preferentially in the MNT stage using mixed acids having a high content of water and oxidation products such as nitrobenzoic acid are formed to a lesser extent. In the DNT stage, the mononitrocresols and dinitrocresols from the MNT stage are preferentially oxidatively degraded by reaction with nitric acid, apart from the reformation of nitrocresols, and the aliphatic hydrocarbons comprised in the toluene are oxidatively degraded by reaction with nitric acid, resulting in formation of CO, $CO_2$ and incompletely oxidized degradation products such as oxalic acid, acetic acid, formic acid, the nitrogen oxides $NO_X$ and $N_2O$ and also traces of hydrocyanic acid.

Thus, it is shown in U.S. Pat. No. 4,361,712 that in the DNT stage, the strong environmental and catalyst poison hydrocyanic acid is also formed in small amounts in addition to other degradation products such as $CO_2$, CO and low molecular weight carboxylic acids by oxidation of the mononitrocresols and dinitrocresols formed in the MNT stage. From an MNT having a content of from 0.3 to 0.6% by weight of mononitrocresols and dinitrocresols, a scrubbing water comprising 86 ppm of HCN is obtained after scrubbing the DNT with water in an acid scrub (scrubbing step I). No information is given about the residual content of hydrocyanic acid in the DNT which has been scrubbed with water.

DNT is usually, according to the prior art, obtained from toluene by reaction with nitric acid in the presence of sulfuric acid (mixed acid) isothermally in two stages in countercurrent to form DNT. However, adiabatic reaction conditions in one or two stages have also been described. Removal of the nitrocresols formed in the MNT stage in a two-stage nitration is usually not carried out, so that, in the process according to the prior art, the nitrocresols are always mostly oxidatively degraded in the DNT stage, forming hydrocyanic acid in small amounts. Hydrocyanic acid is therefore always present in traces of from 30 to 120 ppm in the crude DNT prepared according to the prior art. The actual amount depends on the amount of nitrocresols formed in the MNT stage and the nitrogenation conditions in the DNT stage.

Many of these by-products and degradation products which are formed during the course of the nitration of toluene to form MNT or DNT are highly toxic and act as catalyst poisons in the hydrogenation of the nitrotoluenes to form the corresponding amines. They therefore have to be removed from the nitrotoluene before a catalytic hydrogenation. The crude nitrotoluene is, after the final nitrating acid has been separated off, usually scrubbed in three scrubbing steps, with one scrubbing step being carried out in the presence of alkali at a pH of from 8 to 12. These scrubbing steps according to the prior art are:

1. an acid scrub to remove the dissolved and suspended mineral acids such as sulfuric acid, nitric acid and also nitrogen oxides (acid scrub);
2. an alkaline scrub in the presence of a base (alkaline scrub) such as sodium carbonate (soda), sodium bicarbonate, ammonia, sodium hydroxide or potassium hydroxide (see U.S. Pat. No. 4,482,769, U.S. Pat. No. 4,597,875, U.S. Pat. No. 6,288,289) to remove the weakly acidic impurities dissolved in the crude nitroaromatic, e.g. nitrocresols, nitrobenzoic acids and degradation products from the oxidative degradation of nitrocresols or of aliphatic or cyclic hydrocarbons, for example oxalic acid, hydrocyanic acid, $CO_2$;
3. a neutral scrub to remove residual traces of alkali and to achieve a further reduction in the impurities still present in traces in the product. For this purpose, water is usually used as scrubbing medium and the scrub is carried out as a liquid/liquid scrub at temperatures at which the nitroaromatic to be scrubbed is present as liquid.

It is an object of the invention to provide a process for scrubbing the crude mixture which comprises dinitrotoluene and is obtained in the nitration of toluene after removal of the nitrating acid, which process allows the wastewater from this scrub to be passed directly and without complicated intermediate treatment to separate off or destroy the nitrocresols and nitrobenzoic acids to the biological treatment stage of a water treatment plant. The wastewater treated in the biological stage should, while adhering to all relevant legal requirements, e.g. the requirements of the wastewater regulations of the Federal Republic of Germany, be able to be introduced into an outfall drain. In particular, it is an object of the invention to provide a process for scrubbing the DNT-comprising crude mixture, in which the nitrobenzoic acids (mononitrobenzoic and dinitrobenzoic acids) present in the DNT-comprising crude mixture do not get into the wastewater from the scrub. A further object of the invention is to provide a process of this type in which a "technical grade DNT" n which the known degradation products and potential catalyst poisons which are obtained by oxidative degradation of the nitrocresols in the DNT stage of the nitration and can interfere in the catalytic reduction of DNT by means of hydrogen, e.g. dinitrogen oxide ($N_2O$), nitrogen oxides ($NO_x$) and carbon monoxide (CO), are minimized is obtained after the scrub. A further object of the invention is to remove the hydrocyanic acid dissolved in the crude DNT from the DNT during the course of the scrub to such an extent that no impairment of the reduction of the DNT to form toluenediamine (TDA) in the presence of a catalyst by the hydrocyanic acid still present in the scrubbed DNT can be observed. A further object of the invention is to provide a process in which the content of sulfuric acid, nitric acid and $NO_x$ (as $HNO_2$) in the wastewater to be passed to the water treatment plant is minimized and the content of hydrocyanic acid is reduced to such an extent that trouble-free operation of the water treatment plant in the presence of this wastewater is always ensured.

The object is achieved by a process for scrubbing a crude mixture which is obtained in the nitration of toluene after separating off the nitrating acid and comprises dinitrotoluene, nitric acid, nitrogen oxides and sulfuric acid, which comprises two scrubbing steps (WS-I) and (WS-II), wherein i) in a first scrubbing step (WS-I), the crude mixture is extracted with a scrubbing acid I comprising nitric acid, nitrogen oxides and sulfuric acid in a scrub comprising at least one extraction stage, where the scrubbing acid discharged from the first extraction stage (WS-I-1) of the first scrubbing step (WS-I) has a total acid content of from 10 to 40% by weight and a content of from 80 to 350 ppm of hydrocyanic acid, giving a prescrubbed, dinitrotoluene-comprising crude mixture, ii) in a second scrubbing step (WS-II), the prescrubbed crude mixture is extracted with a scrubbing acid II in a scrub comprising at least one extraction stage, where the scrubbing acid discharged from the first extraction stage (WS-II-1) of the second scrubbing step (WS-II) has a pH of less than or equal to 4, giving a dinitrotoluene-comprising mixture which is essentially free of nitric acid, sulfuric acid, nitrogen oxides and hydrocyanic acid and has a content of not more than 300 ppm of nitric acid and nitrogen oxides, not more than 3 ppm of sulfate and not more than 50 ppm of hydrocyanic acid.

It has surprisingly been found that in the acid scrub according to the invention comprising a first scrubbing step (WS-I) and a second scrubbing step (WS-II) and optionally an extraction stage with stripping 1) the hydrocyanic acid can be scrubbed out from the crude DNT by means of weak to intermediate-strength acids as extractant in such a way that the nitrocresols, nitrobenzoic acids and the other organic impurities from the oxidative degradation of the nitrocresols remain in the crude DNT and a DNT from which the hydrocyanic acid originally present has been virtually completely removed while the nitrocresols and nitrobenzoic acids are still present in their entirety in the DNT is obtained;

2) the second scrubbing step gives a wastewater in which the amount of nitrocresols (dinitrocresols and trinitrocresols) and of nitrobenzoic acids (mononitrobenzoic and dinitrobenzoic acid) and also of oxidative degradation products of the dinitrocresols present are so small that a complicated intermediate treatment according to the prior art for removing them is no longer required;

3) after extraction of the wastewater with toluene to recover the DNT still dissolved and suspended in this wastewater, the cyanide (hydrocyanic acid) dissolved in this wastewater can also be removed by stripping the extracted wastewater to recover the toluene dissolved and suspended therein.

Furthermore, it has been found that the acid scrub according to the invention comprising a first scrubbing step (WS-I) and a second scrubbing step (WS-II) gives, in the second scrubbing step, a wastewater which can be introduced without intermediate treatment for removing nitrocresols (dinitrocresols and trinitrocresols) and nitrobenzoic acids (mononitrobenzoic and dinitrobenzoic acids) and also oxidative degradation products of the dinitrocresols into the biological treatment stage of a water treatment plant. The wastewater obtained after leaving the biological treatment stage can be directly discharged into an outfall drain while adhering to the limit values prescribed in relevant wastewater regulations, for example those of the Federal Republic of Germany. In particular, it was surprising that when the pH in the first extraction stage of the second scrubbing step is adhered to, virtually the entire amount of the nitrobenzoic acids remains in the DNT-comprising organic phase and does not go over into the wastewater.

A BRIEF DESCRIPTION OF THE FIGURES

Figure 1:
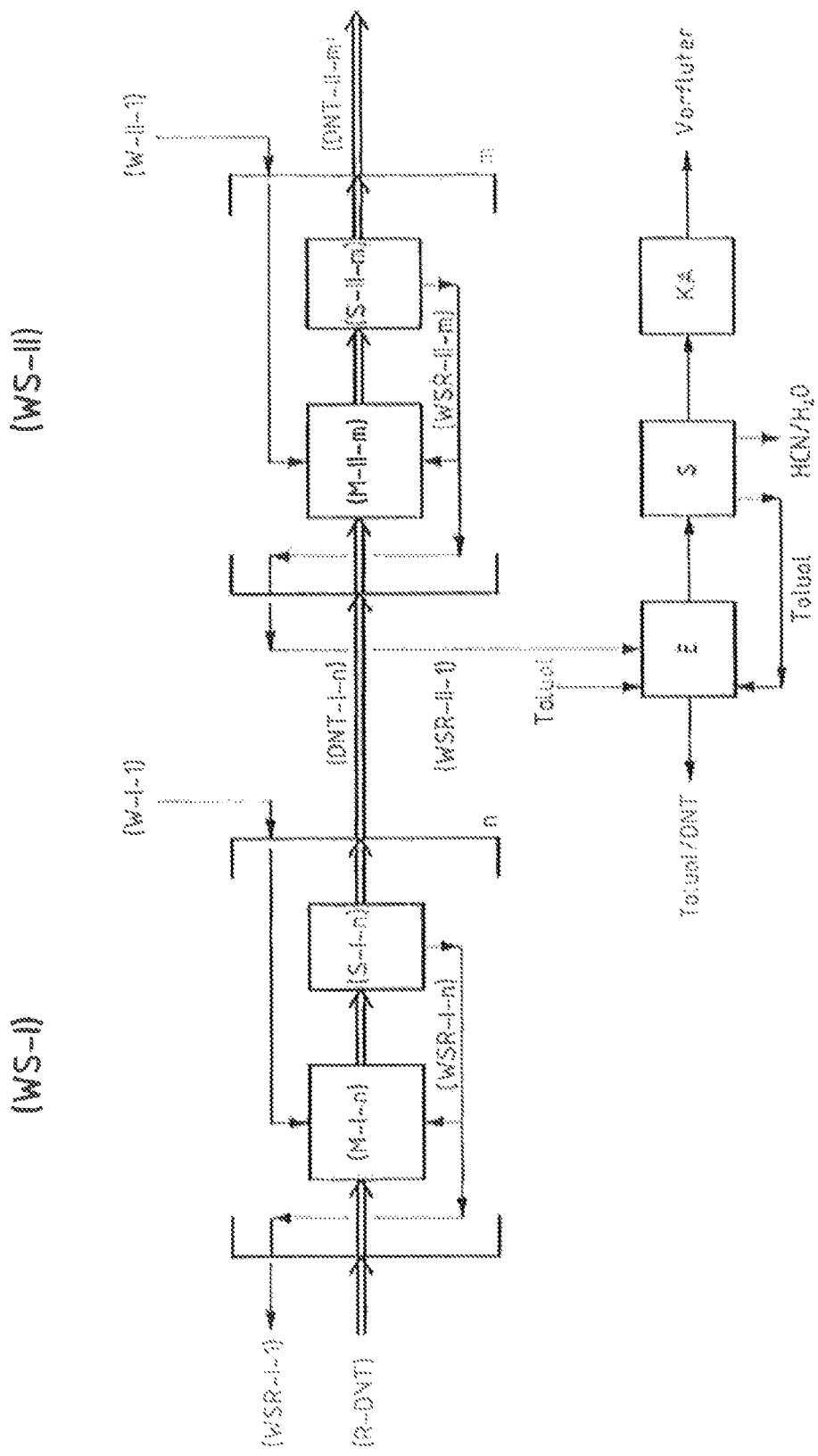
FIG. 1 shows a schematic depiction of a scrub of crude DNT by the process of the invention according to a preferred embodiment of the invention.

In a first scrubbing step (WS-I), the crude mixture is extracted with a scrubbing acid (WSR-I) comprising nitric acid, nitrogen oxides and sulfuric acid in a scrub comprising at least one extraction stage, where the scrubbing acid (WSR-I-1) discharged from the first extraction stage (WS-I-1) of the first scrubbing step (WS-I) has a total acid content of from 10 to 40% by weight and a content of 80-350 ppm of hydrocyanic acid (depending on the ratio of freshly introduced water/crude DNT), giving a prescrubbed, dinitrotoluene-comprising crude mixture.

In a second scrubbing step (WS-II), the prescrubbed crude mixture is extracted with a scrubbing acid (WSR-II) in a scrub comprising at least two extraction stages, where the scrubbing acid (WSR-II-1) discharged from the first extraction stage (WS-II-1) of the second scrubbing step (WS-II) has a pH of less than or equal to 4, giving a dinitrotoluene-comprising mixture which is essentially free of nitric acid, sulfuric acid, nitrogen oxides, hydrocyanic acid. $CO_2$, CO and $N_2O$ and in which the nitrocresols, dinitrophenols and nitrobenzoic acids originally present in the crude DNT are still present.

In the extraction/stripping stage, the scrubbing acid (WSR-II-1) obtained from the scrubbing step (WS-II) is extracted with toluene in order to recover the dissolved and suspended DNT. After phase separation, the water which still comprises dissolved and suspended toluene and has a DNT content of less than 20 ppm, preferably less than 10 ppm and particularly preferably less than 1 ppm, is then stripped with steam or an inert gas. The cyanide present in the acidic wastewater having a pH of ≤4 is separated off together with the toluene and collected in the stripping condensate.

This division of the acid scrub into two separate scrubbing steps in conjunction with an extraction and stripping significantly reduces, compared to the prior art as is described, for example, in U.S. Pat. No. 2,976,320, U.S. Pat. No. 4,482,769 and CA 1 034 603, the pollution of the wastewater with sulfate and especially with nitrate which can be removed from the wastewater only with difficulty.

Pursuant to the EU guideline on integrated reduction and avoidance of environmental pollution (IRE-GL), the process of the invention represents a further development of the best available technologies (BAT) as specified in the BREFs (BAT reference document). The process of the invention not only makes it possible for the total amount of wastewater from a DNT plant to be significantly reduced but also makes it possible to dispense with the comprehensive and technically complicated measures for removing or partly removing the nitrocresols, nitrobenzoic acids and other degradation products from the wastewater.

In the first scrubbing step (WS I), the mineral acids sulfuric acid and nitric acid and also nitrogen oxides dissolved in the DNT-comprising crude mixture are separated off using a scrubbing acid as extractant in an at least single-stage extraction.

The first scrubbing step is preferably carried out in at least two stages and in countercurrent. The at least two-stage countercurrent extraction can in principle be carried out as described in EP 0 279 312, EP 0 736 514 or EP 1 780 195.

In countercurrent, the first scrubbing step is generally carried out as follows:
I) in the first extraction stage (WS-I-1) of the first scrubbing step (WS-I), the crude mixture comprising dinitrotoluene, nitric acid, nitrogen oxides and sulfuric acid is fed together with circulating scrubbing acid (WSR-I-1) from a first phase separation apparatus (S-I-1) belonging to this first extraction stage and excess scrubbing acid (WSR-I-2) from the subsequent extraction stage (WS-I-2) into a first mixer (M-I-1), the scrubbing emulsion formed in the mixer is separated in the first phase separation apparatus (S-I-1) into the scrubbing acid (WSR-I-1) and crude mixture (DNT-I-1) which has been scrubbed once, and
II) the crude mixture (DNT-I-1) which has been scrubbed once is, in the subsequent extraction stage (WS-I-2) of the first scrubbing step (WS-I), fed together with the circulated scrubbing acid (WSR-I-2) from a second phase separation apparatus (S-I-2) belonging to this extraction stage and, when the first scrubbing step (WS-I) comprises more than 2 extraction stages, with excess scrubbing acid (WSR-I-3) from the subsequent extraction stage (WS-I-3) or, when the first scrubbing step comprises precisely 2 extraction stages, with freshly introduced water or scrubbing acid into a second mixer (M-I-2) belonging to this extraction stage, where, when the first scrubbing step comprises more than 2 extraction stages, further extraction steps corresponding to the steps I) and II) are able to follow.

The countercurrent extraction can have up to n extraction stages. Here, the extractant is fed to the last of the n extraction stages (WS-I-n) of the first scrubbing step (WS-I). The introduced extractant which is fed to this last extraction stage can be freshly introduced water or a scrubbing acid having a particular total acid content. In an embodiment of the invention, the extractant fed in is water. In a further embodiment, the extractant fed in is a scrubbing acid having a total acid content in the range from 0.2 to 1.5% by weight. For example, this scrubbing acid can be the vapor condensate from concentration of the scrubbing acid obtained in the first extraction step (WS-I-1) of the first scrubbing stage (WS-I). This generally comprises up to 1.0% by weight of nitric acid and up to 0.3% by weight of sulfuric acid and up to 150 ppm of hydrocyanic acid which all originate from the scrubbing acid (WS-I-1). However, the vapor condensate from the plant for reconcentrating the sulfuric acid from the nitration (SAC plant) comprising up to 2% by weight of total acid (predominantly sulfuric acid) can also be used as scrubbing acid.

The scrubbing acid obtained in the first extraction stage (WS-I-1) in the first scrubbing step generally has a total acid content of from 10 to 40% by weight. This total acid content is the sum of nitric acid, sulfuric acid and nitrogen oxides, with nitrogen oxides being calculated as nitrous acid $HNO_2$.

Surprisingly, from 80 to 350 ppm of hydrocyanic acid which has been scrubbed out of the crude DNT (from 30 to 120 ppm of hydrocyanic acid) and discharged together with the scrubbing acid from (WS-I-1) are additionally dissolved in this scrubbing acid having a content of from 10 to 40%, preferably 20-30% by weight, of mineral acid.

The scrubbing acid obtained from the first extraction stage in the first scrubbing step can be recirculated either directly or after concentration to the nitration of toluene. It can also be introduced into the concentration of the final acid from the first stage of the toluene nitration (mononitrotoluene stage). In this first scrubbing step (WS-I), the contamination of the wastewater obtained in the second scrubbing step with sulfate and nitrate is substantially minimized. The nitrate can be removed from the wastewater only by means of a complicated denitrification stage.

The prescrubbed, DNT-comprising crude mixture obtained after the first scrubbing step generally has a content of sulfate of not more than 300 ppm, preferably not more than 100 ppm and particularly preferably not more than 50 ppm and a content of nitric acid and nitrogen oxides of not more than 5000 ppm, preferably not more than 3000 ppm and particularly preferably not more than 1000 ppm. The residual content of hydrocyanic acid in the prescrubbed DNT is generally from 20 to 90 ppm, preferably from 30 to 70 ppm.

In the second scrubbing step (WS II), the remaining residues of nitric acid, nitrogen oxides and sulfuric acid are scrubbed out from the prescrubbed, DNT-comprising crude mixture by means of an at least one-stage extraction with a scrubbing acid which has only a low content of total acid (essentially nitric acid, nitrogen oxides and sulfuric acid) in such a way that the content of mineral acids and nitrogen oxides in the DNT-comprising crude mixture is reduced to a minimum. The hydrocyanic acid remaining in the prescrubbed DNT, generally from 20 to 70 ppm, is also substantially scrubbed out.

The second scrubbing step is preferably carried out in at least two stages and in countercurrent. The countercurrent extraction can have up to m extraction stages. Here, the extractant is fed to the last of the m extraction stages (WS-II-m) of the second scrubbing step (WS-II). The extractant fed in is generally freshly introduced water.

In countercurrent, the second scrubbing step is generally carried out as follows:

I) in the first extraction stage (WS-II-1) of the second scrubbing step (WS-II), the prescrubbed crude mixture comprising dinitrotoluene is fed together with circulating scrubbing acid (WSR-II-1) from a first phase separation apparatus (S-II-1) belonging to this extraction stage and excess scrubbing acid (WSR-II-2) from the subsequent extraction stage (WS-II-2) into a first mixer (M-II-1) belonging to this extraction stage, the scrubbing emulsion formed in the first mixer is separated in the first phase separation apparatus (S-II-1) into the scrubbing acid (WSR-II-1) and crude mixture (DNT-II-1) which has been scrubbed once, and II) the crude mixture (DNT-II-1) which has been scrubbed once is, in the subsequent extraction stage (WS-II-2) of the second scrubbing step (WS-II), fed together with the circulated scrubbing acid (WSR-II-2) from a second phase separation apparatus (S-II-2) belonging to this second extraction stage and, when the second scrubbing step (WS-II) comprises more than 2 extraction stages, with excess scrubbing acid (WSR-I-3) from the subsequent extraction stage (WS-I-3) or, when the scrubbing step comprises precisely two extraction stages, with freshly introduced water into a second mixer (M-II-2) belonging to this extraction stage of the second scrubbing step (WS-II).

where, when the second scrubbing step comprises more than 2 extraction stages, further extraction steps corresponding to steps I) and II) can follow.

Here, the second scrubbing step is carried out in such a way that essentially the total amount of nitrocresols and nitrophenols and preferably up to 95% by weight of the nitrobenzoic acids originally present in the crude mixture remain in the crude mixture and are not discharged with the scrubbing acid. This is achieved according to the invention by the scrubbing acid discharged from the first extraction stage (WS-II-1) of the second scrubbing step (WS-II) having a pH of less than or equal to 4. The total content of nitrocresols and nitrophenols in the low-concentration scrubbing acid which has a pH of 4 or less and is discharged as wastewater is generally less than 5 ppm and the content of nitrobenzoic acids is generally less than 50 ppm. This wastewater, which now only comprises the scrubbed DNT in solution up to the saturation limit, can be passed either directly or after recovery of dissolved DNT by extraction with toluene and stripping to a water treatment plant without the previously customary and necessary pretreatment to remove the nitrocresols and the nitrobenzoic acids and also toxic oxidative degradation products.

In each of the two scrubbing steps (WS-I) and (WS-II), the scrub is preferably carried out in at least two stages in countercurrent. In an embodiment, the first scrubbing step (WS-I) comprises from 2 to 4 extraction stages (n=2-4). In a further embodiment, the second scrubbing step (WS-II) comprises from 2 to 4 extraction stages (m=2-4). It is also possible for more extraction stages, for example 5 or 6, to be provided per scrubbing step. In an embodiment, each scrubbing step comprises precisely 2 extraction stages.

The amount of extractant or freshly introduced water to be introduced into the last extraction stage of each scrubbing step depends on the total acid content (in WS-I) or the pH (in WS-II) to prevail in the first extraction stage of the respective scrubbing step (WS-I) or (WS-II).

The volume ratio of DNT-comprising crude mixture (organic phase) to scrubbing acid (aqueous phase) which are in direct contact with one another in each scrubbing apparatus is generally selected in the range from 1:4 to 10:1, preferably from 1:3 to 5:1 and particularly preferably from 1:3 to 2:1, in the two scrubbing steps. Depending on the phase ratio and the energy input for dispersing, the mixture can be present as an oil-in-water (O/W) emulsion or as a water-in-oil emulsion (W/O emulsion). These phase ratios can be set by addition of the appropriate amount of extractant to the last extraction stage, but preferably at a defined amount of extractant by circulation of the scrubbing acid after phase separation, with only the excess extractant (corresponding to the amount of extractant freshly introduced into the last extraction stage) being fed or discharged into the preceding extraction stage.

The pH of the scrubbing acid which is taken off from the first extraction stage (WS-II-1) of the second scrubbing step (WS II) is generally in the range from 0 to 3, preferably from 0.5 to 2 and particularly preferably from 0.8 to 1.2. The desired, optimal pH in the first extraction stage of the second scrubbing step can be set via the residual content of nitric acid of the prescrubbed crude mixture originating from the first scrubbing step and/or via the amount of freshly introduced water introduced into the last extraction stage of the second scrubbing step. As an alternative, the desired pH can also be set by addition of a mineral acid, for example the scrubbing acid from the first scrubbing step, or of sulfuric acid or preferably nitric acid.

The amount of freshly introduced water or scrubbing acid which is introduced into the last extraction stage of the first scrubbing step (WS-I) is selected so that the scrubbing acid WSR-I-1 has a total acid concentration of 10-40% by weight, preferably 20-30% by weight.

The amount of freshly introduced water which is introduced into the last extraction stage of the second scrubbing step (WS-II) and thus the ratio of DNT to freshly introduced water can, on a volume basis, vary in the range from 1:2 to 15:1, corresponding to from 1.5 $m^3$ to 0.05 $m^3$ of freshly introduced water per t of DNT, preferably from 1:1 to 7:1, corresponding to from 0.75 $m^3$ to 0.107 $m^3$ of freshly introduced water per t of DNT, and particularly preferably from 1:1 to 2:1, corresponding to from 0.75 $m^3$ to 0.38 $m^3$ of freshly introduced water per t of DNT. Both scrubbing steps are carried out at a temperature above the melting point of DNT, generally at from 60 to 75° C.

As scrubbing apparatuses for the two scrubbing steps, it is possible to use, for example, mixer-settler apparatuses or stirred multistage or pulsed packed columns and sieve tray columns, and also static mixers in combination with tube reactors and suitable separation apparatuses. Both static separators and dynamic separators (centrifigual separators) are suitable for separating the scrubbing dispersion composed of DNT-comprising crude mixture to be scrubbed and scrubbing acid.

The scrubbing acid having a pH of less than or equal to 4, preferably from 0 to 3, particularly preferably from 0.5 to 2 and in particular from 0.8 to 1.2, which is discharged from the first extraction stage (WS-II-1) of the second scrubbing step (WS-II) generally has a content of sulfate of not more than 100 ppm, a content of nitric acid of not more than 2000 ppm and a content of $HNO_2$ of not more than 50 ppm. In addition, it comprises, corresponding to the saturation limit at the prescribed temperature, for example from 800 to 1000 ppm of isomeric dinitrotoluenes. The content of nitrocresols and nitrophenols is generally less than 1 ppm, and the content of nitrobenzoic acids is generally less than 50 ppm.

The content of hydrocyanic acid varies in the range 30-120 ppm, preferably 40-120 ppm and particularly preferably 50-100 ppm. The TOC (total organic carbon) of this wastewater is, for example, only about 1100 mg/l, compared to about 3000 mg/l in a wastewater from the alkaline DNT scrub using sodium carbonate. The COD (chemical oxygen demand) of this wastewater is, for example, only about 3000 mg of O/l, compared to about 6000 mg of O/l in a wastewater from the alkaline DNT scrub using sodium carbonate.

In the extraction/stripping step, the DNT dissolved and suspended in the scrubbing acid (WSR-II-1) having a pH of less than or equal to 4 which has been separated off in the extraction stage (WS-II-1), generally from 800 to 2000 ppm, is recovered from this scrubbing acid by extraction with toluene. In addition, the scrubbing acid (WSR-II-1) can be treated together with the vapor condensate from the concentration of the scrubbing acid (WRS-I-1) from the first scrubbing step (WR-I-n), as described in EP 0 737 514. After the extractant has been separated off from the scrubbing acid (WSR-II-1), from about 100 to 500 ppm of dissolved and suspended toluene remain. This raffinate is subsequently subjected to a stripping treatment in which the dissolved hydrocyanic acid, which is present in amounts of, for example, from 50 to 100 ppm, is also, in addition to from 100 to 500 ppm of dissolved extractant, removed from the wastewater down to a prescribed limit value.

The extraction is preferably carried out in the temperature range from, for example, 60 to 70° C. immediately after the scrubbing acid (WSR-II-1) has been separated off from the scrubbed DNT, so as to avoid precipitation of the dissolved DNT from the DNT-saturated scrubbing acid. The ratio of extractant to scrubbing acid (WRS-II-1) is selected so that removal of the DNT from the scrubbing acid down to the desired limit value can be achieved using a very small number of extraction stages. The weight ratio of extractant to scrubbing acid to be treated can be varied in the range from 1:10 to 1:1, preferably from 1:5 to 1:3. The scrubbing acid (WRS-II-1) or the mixture of scrubbing acid (WRS-II-1) and vapor condensate from the concentration of the scrubbing acid (WRS-I-1) is usually extracted from one to five times, preferably from one to three times. The extraction is usually carried out by the known methods according to the prior art for a liquid/liquid extraction, preferably in countercurrent when more than one extraction stage is required. As extraction apparatuses, it is possible to use mixer/settlers as described, for example, in DE 1 135 425, or stirred or pulsed packed columns and sieve tray columns, and also static mixers in combination with suitable separation apparatuses or columns without energy input can also be used. The toluene separated off after the extraction, which comprises the organic materials which can be extracted from the scrubbing acid, essentially DNT, is recirculated together with the toluene obtained in the subsequent stripping of the extracted scrubbing acid to the nitration.

The stripping of the wastewater to remove the dissolved and suspended extractant toluene and of the cyanide present as hydrocyanic acid at pH ≤4 can be carried out using steam as stripping gas by direct introduction or by distillation (indirect), and also using air or inert gas, preferably nitrogen, with exclusion of oxygen. All types of stripping column are suitable as stripping apparatuses. The ratio of the amount of stripping gas to the amount of wastewater to be stripped is selected so that, firstly, the desired limit values of cyanide and toluene in the stripped wastewater are achieved and that, secondly, the content of cyanide (hydrocyanic acid) in the stripping condensate after toluene has been separated off is only at such a level that nonhazardous handling of this wastewater comprising hydrocyanic acid is possible.

The relatively high cyanide content compared to the wastewater in the stripping condensate can be bound by methods of the prior art, e.g. by addition of formaldehyde, or reduced or else completely removed by electrolytic treatment at suitable electrodes or by addition of oxidants such as hydrogen peroxide, peracids, hypochlorite or ozone in sufficient amount to such an extent that the treated stripping condensate having a residual content of hydrocyanic acid can either be recirculated to the extraction stage or discharged without hazard into a water treatment plant. However, the relatively high cyanide content in the stripping condensate can also be reduced or completely removed by additional stripping of the stripping condensate with air or nitrogen. The stripping condensate which has been freed of excess cyanide is likewise recirculated to the extraction stage. The inert gas stream loaded with hydrocyanic acid is thermally oxidized, e.g. together with the CO-comprising offgas stream from the nitration.

The resulting wastewater after extraction and stripping, which has a pH of ≤4, preferably from 0 to 3, particularly preferably from 0.5 to 2 and in particular from 0.8 to 1.2, generally has a content of sulfate of not more than 100 ppm, a content of nitric acid of not more than 2000 ppm and a content of $HNO_2$ of not more than 50 ppm. In addition, it comprises less than 50 ppm, preferably less than 20 ppm and particularly preferably less than 1 ppm, of isomeric dinitrotoluenes. The content of nitrocresols and nitrophenols is generally less than 1 ppm, and the content of nitrobenzoic acids is generally less than 50 ppm. The content of free hydrocyanic acid is less than 1 ppm, preferably less than 0.5 ppm and particularly preferably less than 0.2 ppm. The TOC (total organic carbon) of this wastewater is, for example, only from about 500 to 600 mg/l, compared to about 1100 mg/l in the scrubbing acid (WRS-II-1). The COD (chemical oxygen demand) of this wastewater is, for example, only about 1500 mg of O/l, compared to about 3000 mg of O/l in the scrubbing acid (WRS-II-1) before the extraction/stripping step.

The scrubbing acid (WRS-II-1) which has been pretreated in this way and also a mixture of scrubbing acid (WRS-II-1) and vapor condensate from the scrubbing acid concentration (WRS-I-1) which has been treated in this way generally satisfies, after neutralization and passage through a biological treatment stage in a water treatment plant, all requirements of the wastewater regulations of the Federal Republic of Germany in respect of toxicity including gene toxicity, determined in accordance with DIN EN ISO 38415 T6 (fish), 11348-2 (luminescent bacteria), 38412 L30 (daphnia), 38412 L33 (algae) and DIN EN ISO 9888 (umu test, gene toxicity).

A DNT which has a residual acidity of generally not more than 300 ppm of nitric acid, a content of hydrocyanic acid of generally not more than 50 ppm, preferably not more than 25 ppm and particularly preferably 10 ppm and very particularly preferably not more than 1 ppm, is taken off from the last extraction stage (WR-II-m) of the second scrubbing step (WS-II). The dinitrogen monoxide content ($N_2O$) is generally not more than 200 ppm, preferably not more than 50 ppm and particularly preferably not more than 25 ppm, the CO content is generally not more than 400 ppm, preferably not more than 200 ppm and particularly preferably not more than 50 ppm of CO, the content of nitrocresols and nitrophenols is generally not more than 800 ppm, the content of nitrobenzoic acids is generally not more than 600 ppm (dinitrobenzoic and mononitrobenzoic acid), the residual content of nitric acid is generally not more than 300 ppm and the sulfate content is generally not more than 3 ppm. The pH is generally from 2 to 4. This DNT and the nitrocresols, nitrophenols and nitrobenzoic acids dissolved therein can be hydrogenated completely and without problems to toluene-diamine (TDA) and the corresponding aminocresols, aminophenols and aminobenzoic acids (diaminobenzoic and monoaminobenzoic acids) by methods of the prior art. The aminocresols, aminophenols and aminobenzoic acids remain in the distillation residue in the distillation of TDA and are disposed of together with this distillation residue.

A further advantage is the greater thermal stability of the DNT which has been subjected according to the invention to an acid scrub. Thus, the temperature at which thermal decomposition commences is in the case of a DNT which has been scrubbed only under acid conditions and comprises, for example, 620 ppm of nitrophenols and nitrocresols and 460 ppm of nitrobenzoic acids is increased by about 20° C. compared to a DNT which has been scrubbed according to the prior art in the presence of sodium carbonate and comprises, for example, less than 20 ppm of nitrophenols and nitrocresols.

To detect the cyanide formed during the course of the nitration of toluene to DNT in the scrubbing acids from (WS-I) and (WS-II), it is possible to employ the method described in DIN 38405-D13. Care should be taken that the limit concentration of interfering materials is adhered to by dilution of the sample before carrying out the analysis. The same applies to the commercial cuvette tests.

FIG. 1 shows a schematic depiction of a scrub of crude DNT by the process of the invention according to a preferred embodiment of the invention.

In the first extraction stage (WS-I-1) (n=1) in the scrubbing step I (WS-I), the crude DNT (R-DNT) from the nitration is, after the DNT final acid has been separated off, fed together with the circulated scrubbing acid (WSR-I-1) from the phase separation apparatus (S-I-1) and together with the excess scrubbing acid (WSR-I-2) from the subsequent extraction stage (WS-I-2) into the mixer (M-I-1) in such a way that the prescribed phase ratio of scrubbing acid to DNT is established. After phase separation of the scrubbing emulsion in the phase separation apparatus (S-I-1) belonging to the extraction stage, the scrubbing acid (WSR-I-1) which has been separated off is recirculated to the mixer (M-I-1) belonging to this stage. The excess scrubbing acid (WSR-I-1) is recirculated either directly or after concentration to the nitration.

The once-scrubbed DNT (DNT-I-1) separated off in the separator (S-I-1) is, in the subsequent extraction stage (WS-I-2) (n=2), fed together with the circulated scrubbing acid (WSR-I-2) from the phase separation apparatus (S-I-2) and together with the excess scrubbing acid (WSR-I-3) from the subsequent extraction stage (WS-I-3) into the mixer (M-I-2) in such a way that the prescribed phase ratio of scrubbing acid to DNT is established. After phase separation of the scrubbing emulsion in the phase separation apparatus (S-I-2) belonging to this extraction stage, the scrubbing acid (WSR-I-2) which has been separated off is recirculated to the mixer (M-I-2) belonging to the stage. The excess scrubbing acid (MSR-I-2) is fed into the preceding extraction stage (WS-I-1). The twice-scrubbed DNT (DNT-I-2) which has been separated off in the phase separation apparatus (S-I-2) is transferred into the next extraction stage (WS-I-3) (n=3) for a third scrub. The number of extraction stages can preferably be up to four (n=4). Freshly introduced water or preferably the vapor condensate from the concentration of the scrubbing acid from the scrubbing stage (WS-I-1) is fed as scrubbing medium (W-I-1) into the last extraction stage (WS-I-4) in such an amount that the scrubbing acid separated off from (S-I-1) has a total acid content of from 20 to 40%.

The prescrubbed DNT (DNT-I-n) from scrubbing step (WS-I) is, in the first extraction stage (WS-II-1) (m=1) in the scrubbing step (WS-II), fed together with the circulated scrubbing acid (WSR-II-1) from the phase separation apparatus (S-II-1) and together with the excess scrubbing acid (WSR-II-2) from the subsequent extraction stage (WS-II-2) into the mixer (M-II-1) in such a way that the prescribed phase ratio of scrubbing acid to DNT is established. After phase separation of the scrubbing emulsion in the phase separation apparatus (S-II-1) belonging to the scrubbing stage, the scrubbing acid (WSR-II-1) which has been separated off is recirculated to the mixer (M-II-1) belonging to this stage. The excess scrubbing acid (WSR-II-1) is subsequently treated further in the extraction and stripping steps according to the invention in order to recover the product (DNT) dissolved therein.

The once-washed DNT (DNT-II-1) separated off in the phase separation apparatus (S-II-1) is, in the subsequent extraction stage (WS-II-2) (m=2), fed together with the circulated scrubbing acid (WSR-II-2) from the phase separation apparatus (S-II-2) and the excess scrubbing acid (WSR-II-3) from the subsequent scrubbing stage (WS-II-3) into the mixer (M-II-2) in such a way that the prescribed phase ratio of scrubbing acid to DNT is established. After phase separation of the scrubbing emulsion in the phase separation apparatus (S-II-2) belonging to this extraction stage, the scrubbing acid (WSR-II-2) which has been separated off is fed into the mixer (M-II-2) belonging to this stage. The excess scrubbing acid (WSR-II-2) is fed into the preceding extraction stage (WS-II-1). The twice-scrubbed DNT (DNT-II-2) separated off in the phase separation apparatus (S-II-2) is transferred into the next extraction stage (WS-II-3) (m=3) for a third scrub. The number of extraction stages can preferably be up to six (m=6). Freshly introduced water is fed as scrubbing medium (W-II-1) into the last extraction stage (WS-II-6) in such an amount that the scrubbing acid separated off from (S-II-1) has a pH of preferably from 0 to 3. The pH in the first extraction stage (WS-II-1) can additionally be adjusted subsequently to the optimal operating value by addition of nitric acid or scrubbing acid (WSR-I-1).

The excess scrubbing acid (WSR-II-1) from the first extraction stage (WS-II-1) is subsequently treated with toluene in an extraction apparatus in extraction step (E). After phase separation of the extraction mixture of toluene/(WSR-II-1), this toluene is fed together with the dissolved DNT into the nitration. The scrubbing acid comprising toluene which is still dissolved and traces of suspended toluene and the cyanide is freed of this toluene together with the cyanide in the stripping step (S). The scrubbing acid which has been freed of toluene and cyanide is, after neutralization, discharged directly into a biological treatment stage of a water treatment plant. The toluene separated off during stripping is recirculated to the extraction. The hydrocyanic acid present in increased concentration in the stripping condensate can be destroyed according to the prior art, e.g. by treatment with oxidants.

Figure 2:
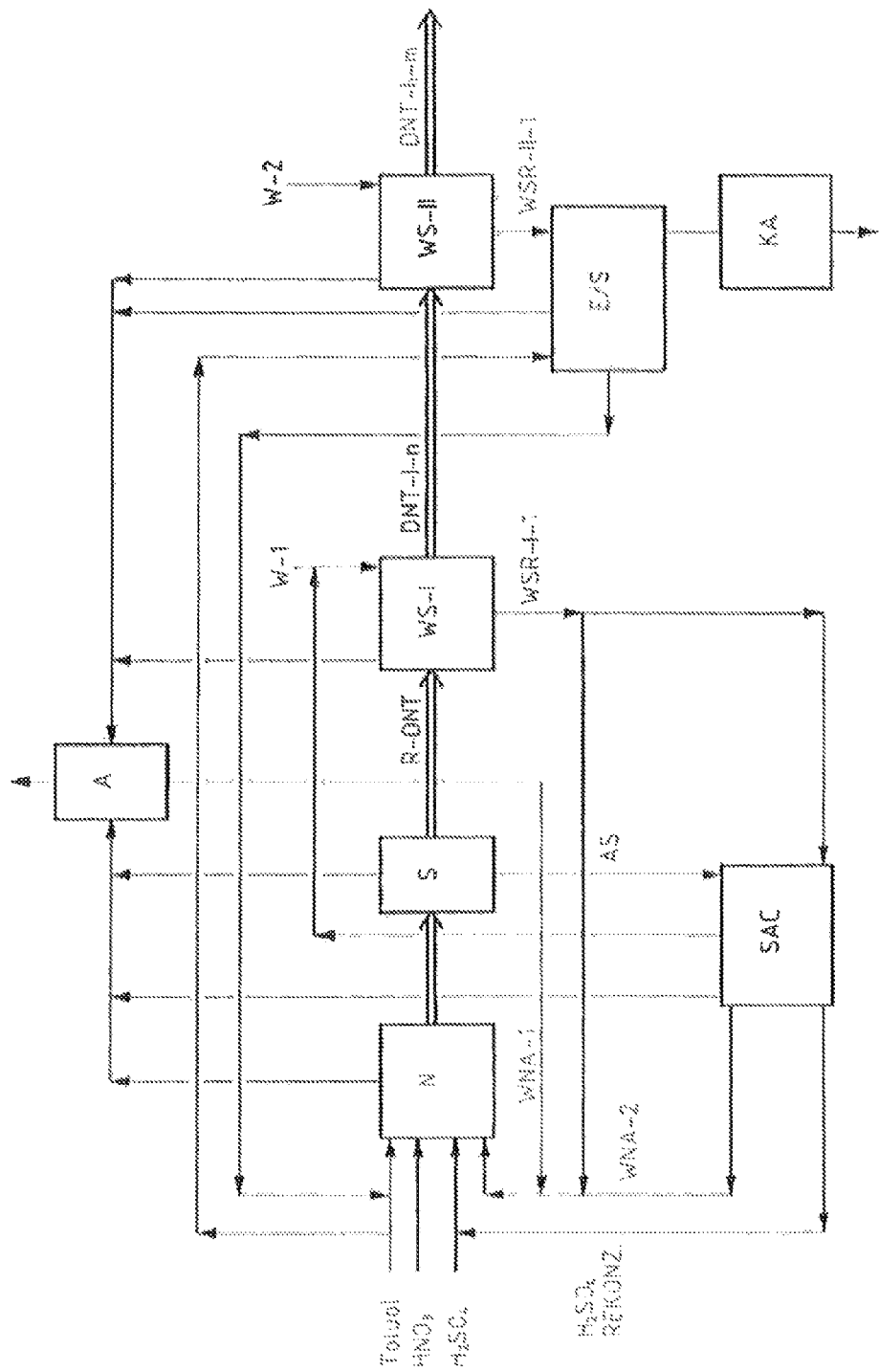
FIG. 2 shows a schematic depiction of a production plant according to the invention for the nitration of toluene to DNT with subsequent scrubbing according to the invention of the crude DNT in two steps according to a preferred embodiment of the invention.

FIG. 2 shows a schematic depiction of a production plant according to the invention for the nitration of toluene to DNT with subsequent scrubbing according to the invention of the crude DNT in two steps according to a preferred embodiment of the invention.

The dinitrotoluene isomer mixture formed in the nitration unit (N) by means of a two-stage continuous isothermal or adiabatic nitration of toluene in a mixture of sulfuric acid and nitric acid in countercurrent is, after separation of the nitration emulsion in the phase separation apparatus (separator (S)) fed into a scrub according to the invention having two scrubbing steps (WS-I) and (WS-II). In scrubbing step (WS-I), the mineral acids sulfuric acid, nitric acid and nitrogen oxides dissolved in the crude DNT are scrubbed out. The scrubbing acid (WSR-I-1) separated off from the first scrubbing stage (WS-I-1) in this scrubbing step, which has a total acid content of 10-40% by weight, is recirculated directly to the nitration unit (N) or, after further concentration, as (WNA-2) to the nitration. The vapor condensate from the concentration of the scrubbing acid (WRS-I-1) and/or the final nitrating acid is/are recirculated as scrubbing water (W-1) to the scrubbing step (WS-I).

In the second scrubbing step (WS-II), the residues of mineral acids still remaining in the prescrubbed DNT from (WS-I) are scrubbed out in such a way that a scrubbing acid (WSR-II-1) having a pH in the range of preferably from 0 to 3 results. To supplement the amount of scrubbing acid which has been separated off, freshly introduced water is added in (WS-II). This scrubbing acid from scrubbing step II (WS-II) is, to recover the DNT dissolved therein and remove the cyanide, treated in the extraction/stripping process step (E/S) in such a way that it can, after neutralization, be introduced directly into a biological after-treatment stage in a water treatment plant (KA).

The final nitrating acid obtained in the separation unit (S) is concentrated to sulfuric acid (up to 96%) in a concentration plant for sulfuric acid (SAC) and recirculated to the nitration. The nitric acid (WNA-1) recovered from the nitrogen oxide-comprising offgases from nitration and scrubbing collected in the offgas treatment (A) is recirculated together with the scrubbing acid (WSR-I-1) obtained from scrubbing step (WS-I) or, after concentration, as (WNA-2) likewise to the nitration.

The present invention is illustrated by the following examples.

EXAMPLES

Example 1

According to the Prior Art 4500 kg/h of DNT having a residual content of 0.94% by weight of sulfuric acid, 1.43% by weight of nitric acid and 1.15% by weight of nitrogen dioxide were, after the final nitrating acid had been separated off, scrubbed in countercurrent in 2 stages in an acid scrub (scrubbing step I). In the first extraction stage, scrubbing was carried out using a scrubbing acid comprising 7.58% by weight of sulfuric acid, 19.52% by weight of nitric acid and about 0.45% by weight of nitrogen oxides (as $HNO_2$) in a phase ratio of DNT to scrubbing acid of 1:1. In the second extraction stage of the scrubbing step I, scrubbing was likewise carried out at a phase ratio of 1:1 using a scrubbing acid comprising not more than 0.5% by weight of sulfuric acid, about 6% by weight of nitric acid and about 0.15% by weight of nitrogen oxides. The amount of added water or condensate from the further concentration of the scrubbing acid (in the present example of about 450 l/h) fed to the last extraction stage is selected so that the concentration of the scrubbing acid in the first extraction stage of the acid scrub, in contact with the crude DNT to be scrubbed, does not exceed the laid-down acid strength and density. To maintain the prescribed phase ratio, the scrubbing acid separated off in the separator (phase separation apparatus) of the respective extraction stage was circulated and only the excess was transferred to the preceding scrubbing stage or discharged.

The scrubbing acid discharged from the acid scrub, which had a total acid content of 27.55% by weight, was, after further concentration, recirculated to the nitration.

The DNT from the acid scrub, which was virtually free of mineral acids, was freed of the residues of the mineral acids still dissolved in the prescrubbed DNT, mainly nitric acid and $NO_x$, and entrained scrubbing acid, the nitrophenols and nitrocresols, nitrobenzoic acids and all other strong and weak acids from the oxidation of the nitrocresols and dinitrocresols in the DNT stage, e.g. oxalic acid, acetic acid, formic acid, hydrocyanic acid, carbon dioxide, etc, in the alkaline scrub.

About 4350 kg of prescrubbed DNT from scrubbing step I (acid scrub) having a residual content of not more than 100 ppm of sulfuric acid and not more than 3000 ppm of nitric acid/nitrogen oxides were scrubbed in an alkaline scrubbing step (alkali scrub) in the presence of a base (sodium carbonate) in a phase ratio of 1:1 in one stage, with a pH of 9-10 being established. After phase separation of the scrubbing emulsion from the alkali scrub, the DNT which had been separated off was additionally scrubbed in a one-stage neutral scrub, likewise at a phase ratio of 1:1, to free it of entrained traces of the alkali scrub by addition of freshly introduced water (in the present case 2800 l/h). After phase separation, the scrubbing water separated off in the neutral scrub is fed as scrubbing water into the alkali scrub. To maintain the prescribed phase ratios in the two scrubbing steps (alkali scrub and neutral scrub), the scrubbing water separated off in the separator of the respective scrubbing stage was circulated and only the excess was transferred from the neutral scrub to the alkali scrub or discharged from the alkali scrub.

The alkaline scrubbing liquor discharged from the alkali scrub, which had a pH of 9-10 and a content of 40 ppm of sulfate, 580 ppm of nitrate, 2500 ppm of nitrite, 990 ppm of DNT and 740 ppm of trinitrocresols, was fed directly into a thermolysis at 290° C. and 90 bar in order to decompose the nitrophenols and nitrocresols and also further nitro compounds and the dissolved DNT. The water discharged from the thermolysis, in which the nitrophenols and nitrocresols, nitrobenzoic acids, hydrocyanic acid and the dissolved DNT had been decomposed, was subjected to an additional biological after-treatment in a water treatment plant before release into the outfall drain.

Example 2

According to the Invention 4500 kg/h of DNT having a residual content of 0.94% by weight of sulfuric acid, 1.43% by weight of nitric acid, 1.15% by weight of nitrogen dioxide and an average of 70 ppm of hydrocyanic acid were, after the final nitrating acid had been separated off, scrubbed in countercurrent in 2 stages in scrubbing step I (WS-I). In the first extraction stage (WS-I-1), scrubbing was carried out using a scrubbing acid comprising 7.58% by weight of sulfuric acid, 19.52% by weight of nitric acid, about 0.45% by weight of nitrogen oxides (as $HNO_2$) and an average of 250 ppm of hydrocyanic acid at a phase ratio of DNT to scrubbing acid of 1:1. In the second extraction stage (WS-I-2) of the scrubbing step I, scrubbing was likewise carried out at a phase ratio of 1:1 using a scrubbing acid comprising not more than 0.5% by weight of sulfuric acid, about 6% by weight of nitric acid, about 0.15% by weight of nitrogen oxides and an average of 150 ppm of hydrocyanic acid (vapor condensate). The amount of added water or condensate from the further concentration of the scrubbing acid (in the present example about 450 l/h) which was fed into the last extraction stage is selected so that the concentration of the scrubbing acid in the first extraction stage (WS-I-1) in contact with the crude DNT to be scrubbed does not exceed the laid-down acid strength and density. To maintain the prescribed phase ratio, the scrubbing acid separated off in the separator (phase separation apparatus) of the respective extraction stage was circulated and only the excess was transferred to the preceding scrubbing stage or discharged.

The scrubbing acid discharged in the scrubbing step (WS-I), which had a total acid content of 27.55% by weight, was, after further concentration, recirculated to the nitration.

The prescrubbed DNT which had been virtually completed freed of the mineral acids in the scrubbing step (WS-I) was freed of the residues of the mineral acids still dissolved in the DNT, mainly nitric acid and $NO_x$ and hydrocyanic acid or entrained scrubbing acid from scrubbing step I (WS-I), in scrubbing step II (WS-II).

About 4350 kg of prescrubbed DNT from scrubbing step I (WS-I), which had a residual content of not more than 100 ppm of sulfuric acid, not more than 3000 ppm of nitric acid/nitrogen oxides and an average of 50 ppm of hydrocyanic acid, were scrubbed in countercurrent in two stages. In the first extraction stage of scrubbing step II (WS-II), scrubbing was carried out using a scrubbing acid having a pH of from 0 to 3, particularly preferably from 0.8 to 1.2, at a phase ratio of DNT:scrubbing acid of 1:1. In the second extraction stage of scrubbing step II (WS-II), scrubbing was likewise carried out at a phase ratio of 1:1 using a scrubbing acid which comprised only traces of mineral acid, especially nitric acid. The amount of freshly introduced water added (in the present example about 2800 l/h), which was fed into the last extraction stage (WS-II-n) (n=2), was selected so that the pH in the first extraction stage (WS-II-1), in which the DNT was extracted from the scrubbing step I (WS-I) was maintained at the laid-down optimal value for the pH in the range from 0.8 to 1.2. To maintain the prescribed phase ratios in the extraction stages, the scrubbing acid separated off in the separator of the respective extraction stage was circulated and only the excess was transferred to the preceding stage or discharged.

The scrubbing acid (about 2800 l) discharged from the first extraction stage (WS-II-1) in scrubbing step II (WS-II), which had a pH of 1.0 and a content of 85 ppm of sulfuric acid, 1800 ppm of nitric acid, 40 ppm of nitrogen oxides, 980 ppm of DNT, less than 1 ppm of trinitrocresols, less than 10 ppm of nitrobenzoic acids and an average of 80 ppm of hydrocyanic acid, was extracted with toluene in a plurality of stages at a phase ratio (volume) of toluene to water of 1:3. After phase separation, the toluene extract was recirculated together with the DNT to the nitration. The scrubbing acid (raffinate) after the extraction with toluene comprised less than 1 ppm of DNT, an average of up to 500 ppm of toluene and about 80 ppm of hydrocyanic acid. Toluene and hydrocyanic acid were separated off in multistage stripping with steam, optionally assisted by an inert gas stream. Both toluene and hydrocyanic acid were present in an increased concentration in the condensate. The toluene which had been separated off was recirculated to the extraction. The cyanide present in increased concentration (e.g. by a factor of 10) in the stripping condensate was decomposed by treatment with oxidants as per the prior art. This treated condensate, which was essentially free of cyanide, was recirculated to the extraction. The scrubbing acid, which was free of toluene and cyanide (max. 0.2 ppm), was, after neutralization to a pH of 7-8, fed directly into a biological after-treatment. The wastewater obtained after this biological treatment satisfied all requirements in respect of toxicity laid down in the wastewater regulations of the Federal Republic of Germany.

The invention claimed is:

1. A process for scrubbing a crude mixture which is obtained in the nitration of toluene after separating off the nitrating acid and comprises dinitrotoluene, nitric acid, nitrogen oxides and sulfuric acid, which comprises two scrubbing steps (WS-I) and (WS-II), wherein
   i) in a first scrubbing step (WS-I), the crude mixture is extracted with a scrubbing acid I comprising nitric acid, nitrogen oxides and sulfuric acid in a scrub comprising at least one extraction stage, where the scrubbing acid discharged from the first extraction stage (WS-I-1) of the first scrubbing step (WS-I) has a total acid content of from 10 to 40% by weight and a content of from 80 to 350 ppm of hydrocyanic acid, giving a prescrubbed crude mixture,
   ii) in a second scrubbing step (WS-II), the prescrubbed crude mixture comprising dinitrotoluene is extracted with a scrubbing acid II in a scrub comprising at least one extraction stage, where the scrubbing acid discharged from the first extraction stage (WS-II-1) of the second scrubbing step (WS-II) has a pH of less than or equal to 4 and a content of sulfate of not more than 100 ppm, a content of nitric acid of not more than 2000 ppm, a content of nitrogen oxides (calculated as $HNO_2$) of not more than 50 ppm and a content of hydrocyanic acid of not more than 120 ppm, giving a dinitrotoluene-comprising mixture which is essentially free of nitric acid, sulfuric acid, nitrogen oxides and hydrocyanic acid and has a content of not more than 300 ppm of nitric acid and nitrogen oxides, not more than 3 ppm of sulfate and not more than 50 ppm of hydrocyanic acid.

2. The process according to claim 1, wherein the first scrubbing step (WS-I) comprises from 2 to 4 extraction stages and is carried out in countercurrent.

3. The process according to claim 1, wherein the second scrubbing step (WS-II) comprises from 2 to 6 extraction stages and is carried out in countercurrent.

4. The process according to claim 1, wherein the scrubbing acid discharged from the first extraction stage (WS-II-1) of the second scrubbing step (WS-II) has a pH of from 0 to 3.

5. The process according to claim 1, wherein the scrubbing acid discharged from the first extraction stage (WS-II-1) of the second scrubbing step (WS-II) has a pH of from 0.5 to 2.

6. The process according to claim 1, wherein water or a scrubbing acid having a total acid content of from 0.2 to 1.5% by weight is fed to the last extraction stage (WS-I-n) of the first scrubbing step (WS-I).

7. The process according to claim 1, wherein water is fed to the last extraction stage (WS-II-n) of the second scrubbing step (WS-II).

8. The process according to claim 1, wherein
   I) in the first extraction stage (WS-I-1) of the first scrubbing step (WS-I), the crude mixture comprising dinitrotoluene, nitric acid, nitrogen oxides and sulfuric acid is fed together with circulating scrubbing acid (WSR- I-1) from a first phase separation apparatus (S-I-1) belonging to this first extraction stage and excess scrubbing acid (WSR-I-2) from the subsequent extraction stage (WS-I-2) into a first mixer (M-I-1), the scrubbing emulsion formed in the mixer is separated in the first phase separation apparatus (S-I-1) into the scrubbing acid (WSR-I-1) and crude mixture (DNT-I-1) which has been scrubbed once, and II) the crude mixture (DNT-I-1) which has been scrubbed once is, in the subsequent extraction stage (WS-I-2) of the first scrubbing step (WS-I), fed together with the circulated scrubbing acid (WSR-I-2) from a second phase separation apparatus (S-I-2) belonging to this extraction stage and, when the first scrubbing step (WS-I) comprises more than 2 extraction stages to (WS-I-n), with excess scrubbing acid (WSR-I-3) (WSR-I-n) from the subsequent extraction stage (WS-I-3) to (WS-I-n) or, when the first scrubbing step comprises precisely 2 extraction stages, with freshly introduced water or scrubbing acid (W-I-1) into a second mixer (M-I-2) belonging to this extraction stage.

9. The process according to claim 1, wherein

I) in the first extraction stage (WS-II-1) of the second scrubbing step (WS-II), the prescrubbed crude mixture comprising dinitrotoluene is fed together with circulating scrubbing acid (WSR-II-1) from a first phase separation apparatus (S-II-1) belonging to this extraction stage and excess scrubbing acid (WSR-II-2) from the subsequent extraction stage (WS-II-2) into a first mixer (M-II-1) belonging to this extraction stage, the scrubbing emulsion formed in the first mixer is separated in the first phase separation apparatus (S-II-1) into the scrubbing acid (WSR-II-1) and crude mixture (DNT-II-1) which has been scrubbed once, and II) the crude mixture (DNT-II-1) which has been scrubbed once is, in the subsequent extraction stage (WS-II-2) of the second scrubbing step (WS-II), fed together with the circulated scrubbing acid (WSR-II-2) from a second phase separation apparatus (S-II-2) belonging to this second extraction stage and, when the second scrubbing step (WS-II) comprises more than 2 extraction stages to (WS-II-m), with excess scrubbing acid (WSR-II-3) to (WSR-II-m) from the subsequent extraction stage (WS-II-3) to (WS-II-m) or, when the scrubbing step comprises precisely two extraction stages, with freshly introduced water (W-II-1) into a second mixer (M-II-2) belonging to this extraction stage of the second scrubbing step (WS-II).

10. The process according to claim 1, wherein the volume ratio of dinitrotoluene-comprising crude mixture and scrubbing acid in the extraction stages of the scrubbing steps (W-I) and (W-II) is from 1:4 to 10:1.

11. The process according to claim 1, wherein the volume ratio of dinitrotoluene-comprising crude mixture to freshly introduced water in the last extraction stage (W-II-m) of the second scrubbing step (W-II) is from 1:2 to 15:1.

12. The process according to claim 1, wherein a dinitrotoluene-comprising mixture which comprises a total of not more than 800 ppm of nitrocresols and nitrophenols, not more than 600ppm of nitrobenzoic acids, not more than 300 ppm of nitric acid, not more than 50 ppm of hydrocyanic acid and not more than 3 ppm of sulfate is taken off from the last extraction stage (WS-II-m) of the second scrubbing step (WS-II).

13. The process according to claim 1, wherein the scrubbing acid discharged from the first extraction stage (WS-II-1) of the second scrubbing step (WS-II) has a total content of nitrocresols and nitrophenols of less than 5 ppm and a content of nitrobenzoic acids of less than 50 ppm.

14. The process according to claim 12, wherein the scrubbing acid discharged from the first extraction stage (WS-II-1) of the second scrubbing step (WS-II) is after dinitrotoluene dissolved therein has been separated off by extraction and the extractant has been separated off and after neutralization, fed without further pretreatment to the biological treatment stage of a water treatment plant.

15. The process according to claim 14, wherein the scrubbing acid which has been separated off from the first extraction stage (WS-II-1) of the second scrubbing step (WS-II) is extracted with toluene and the extracted scrubbing acid is stripped with a stripping gas, giving a wastewater having a hydrocyanic acid content of less than 1 ppm.

* * * * *